United States Patent
Li

(10) Patent No.: US 6,197,818 B1
(45) Date of Patent: Mar. 6, 2001

(54) DRUG FOR TREATING DIABETIC NEPHROSIS

(75) Inventor: Leishi Li, Nanjing (CN)

(73) Assignee: Nanjing General Hospital of Nanjing Command, PLA (CN)

( * ) Notice: Subject to any disclaimer, the term of this patent is extended or adjusted under 35 U.S.C. 154(b) by 0 days.

(21) Appl. No.: 09/319,086

(22) PCT Filed: Sep. 1, 1998

(86) PCT No.: PCT/CN98/00175

§ 371 Date: Oct. 25, 1999

§ 102(e) Date: Oct. 25, 1999

(87) PCT Pub. No.: WO99/16432

PCT Pub. Date: Apr. 8, 1999

(51) Int. Cl.[7] ................................................. A61K 31/225
(52) U.S. Cl. ............................................................ 514/548
(58) Field of Search .............................................. 514/548

(56) References Cited

U.S. PATENT DOCUMENTS 5,652,265 * 7/1997 Vittori et al. ......................... 514/548

FOREIGN PATENT DOCUMENTS 2-149515   8/1990   (JP) .

OTHER PUBLICATIONS

Debord, et al., "Influence Of Renal Function On The Pharmacokinetics Of Diacerein After A Single Oral Dose" *Fundam. Clinical Pharmacol.*, vol. 7 (8) 1993, pp. 435–441 (Abstract only).

Zheng, et al., "Effect of Rheum Officinal on the Proliferation of Renal Tubular Cells in Vitro" *National Medical Journal of China*, vol. 73, (6), 1993, pp. 343–345 (Abstract).

Leishi, et al., "Rheum Officinale: A New Lead in Preventing Progression of Chronic Renal Failure," *Chinese Medical Journal*, vol. 109 (1), 1996, pp. 35–37.

* cited by examiner

Primary Examiner—Theodore J. Criares
Assistant Examiner—Jennifer Kim
(74) *Attorney, Agent, or Firm*—McDonnell Boehnen; Hulbert & Berghoff

(57) ABSTRACT

The present invention relates new use of rhein or the salt thereof, that is new use in preparing medicine for treatment of diabetic nephropathy. A medicine containing rhein or the salt thereof for treatment of diabetic nephropathy may be supplied in aqueous solution or capsule for oral, the dosage is not larger than 200 mg/day. Toxicity of rhein or the salt thereof is low, LD50 is 3.2 g/kg. The concentration of medicine in blood is still higher in 24 hours after administered rhein by oral. Rhein can effectively control or decrease the hyperglycemia, suppress renal hypertrophy and kidney index in experimental diabetic rats. The urinary protein execretion was significantly decreased in the diabetic patients treated by rhein.

4 Claims, No Drawings

DRUG FOR TREATING DIABETIC NEPHROSIS

TECHNICAL FIELD

The present invention relates to an anthraquinone carboxylic acid or the salt thereof, especially to the use of rhein or the salt thereof, more particularly the use in preparing medicine.

BACKGROUND OF THE INVENTION

Diabetes is a frequently occurring disease, and the main medicament for its treatment is insulin at present. However, insulin has no therapeutic effect to the kidney damage caused by diabetes, such as renal hypertrophy, although it can decrease the urinary glucose. Until now, no report has been found on the medicine for treatment of renal hypertrophy caused by diabetes and no effective medicine has been found for treatment of diabetic nephropathy.

SUMMARY OF THE INVENTION

The object of the present invention is to provide a new use of rhein or the salt thereof, that is the new application in preparing medicine.

Actually the present invention relates to the application of rhein or the salt thereof in preparing medicine for treatment of diabetic nephropathy.

The present invention provides a medicine of low toxicity for treatment of diabetic nephropathy.

The general formula of rhein or the salt thereof can be shown as the following:

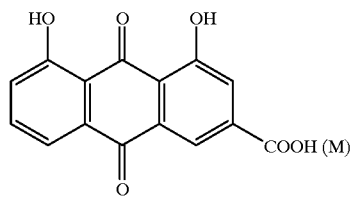

wherein M represents sodium or potassium.

The preparation of the medicine containing rhein or the salt thereof is very simple, in which the rhein or the salt thereof is grounded into power and then prepared into capusula or aqueous solution for oral. The dosage of rhein is not larger than 200 mg/day and may be given twice or thrice by oral.

DETAILED DESCRIPTION OF THE INVENTION

The present invention relates to new application of rhein or the salt thereof in preparing medicine for treatment of diabetic nephropathy.

The object of the present invention is to provide a new use of rhein or the salt thereof in preparing medicine for treatment of diabetic nephropathy. The present invention provides a medicine of low toxicity for treatment of diabetic nephropathy.

Rhubarb (*Rheum Officinale*, a Chinese herb) is a particular medicine in China and has been commonly used as a laxative for many years in traditional Chinese medicine. It has been found that rhubarb is valuable in preventing progression of chronic renal failure. Rhein is a major component of anthraquinones extracted from rhubarb. It has been known that rhein possesses effects on anti-bacterial, anti-inflammatory, and anti-tumor et al.

Rhein is a needle-like yellow crystal with melting point of 318–320° C., and soluble slightly in water but soluble in organic solvent. It remains steady in room temperature for more than one year. The general formula of rhein or the salt thereof is shown as the following:

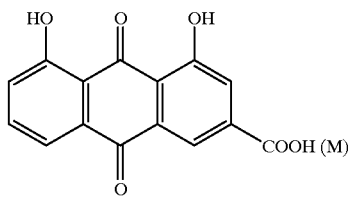

wherein M represents sodium or potassium.

As a natural product, rhein is of low toxicity and safe for therapy. The half lethal dose ($LD_{50}$) is 3.2 g/Kg for SD rats.

There are not marked gastro-intestinal reactions caused by the oral route of rhein in volunteers treated by rhein. Of the thirty-six volunteers given rhein at dose of 200 mg/day (100 mg, b.i.d) for 3 days, only 5 persons experience gastro-intestinal disorders. Diarrhea occurred twice or thrice a day in three of these persons, and four times in only one person.

In pharmacolinetical study, rhein can be easily absorbed from gastro-intestinal trace after the agent is given orally, and the blood concentration of rhein maintains for a longer period. The blood level of rhein reaches peak in one and half hours to three hours after one single dose of rhein at 200 mg in health man. The blood level of rhein still kept at 200 to 500 ng/ml at 24th hour in volunteers.

Thus, rhein possesses advantageous as medicine.

As shown in further investigation of rhein, hyperglycemia in experimental diabetic rats can be controlled or reduced effectively by rhein or sodium rheinate given orally. Particularly rhein is able to control or suppress renal hypertrophy, and decrease the kidney index (kidney weight/body weight ratio) obviously in diabetic rats. Rhein also can ameliorate the urinary albumin excretion significantly in diabetic nephropathy patients.

The medicine containing rhein or the salt thereof for treatment of diabetic nephropathy may be supplied in capsula or solution for oral.

A dosage of rhein up to 200 mg/day is feasible, and may be given twice or thrice a day.

The following Examples will illustrate the present invention in more details.

EXAMPLE 1

Suppression of Renal Hypertrophy by Rhein in Experiment Diabetic Rats

Drug: Rhein, a needle-like yellow crystal with melting point of 318–320°C., was prepared into aqueous solution for oral. The concentration of rhein is 0.2 g/L.

Diabetic animal model of rat: Adult female SD rats (Experimental Animal Center, Jinling Hospital, Nanjing) with body weights of 200 to 250 grams were used. Rats were made diabetic by an intra-abdominal injection of Streptozotocin (Sigma Chemical Co.; in 0.1 mmol/L citrate buffer, pH 4.5) in a dose of 25 mg/Kg/day for 5 days. Only rats with blood glucose level within the range of 13 to 25 mmol/L were recognized as the establishment of the diabetic model.

The observation was focused on the changes of kidney weight and volume in diabetic rats treated by rhein.

The experiment was designed as the following:

|  | Normal rats | | Diabetic rats | |
| --- | --- | --- | --- | --- |
|  | Control | Rhein-treated | Control | Rhein-treated |
| No. of animals | 8 | 7 | 7 | 6 |
| Dosage of Rhein: mg/Kg/day | 0 | 2 | 0 | 2 |
| Distilled water: ml/Kg/day | 5 | 5 | 5 | 5 |

The experimental results are listed in the following tables.

|  | Normal rats | | Diabetic rats | |
| --- | --- | --- | --- | --- |
|  | Control | Rhein-treated | Control | Rhein-treated |
| 1. Effect of rhein on the changes of the blood glucose levels (mmol/L) | | | | |
| Pre-diabetic | 6.62 ± 0.84 | 6.12 ± 0.34 | 5.62 ± 1.84 | 6.23 ± 0.44 |
| After diabetic (weeks) | | | | |
| 1 | 6.00 ± 0.44 | 5.92 ± 0.54 | 19.82 ± 2.84 | 20.32 ± 1.89 |
| 4 | 6.31 ± 0.36 | 5.66 ± 0.84 | 21.12 ± 2.19 | 19.77 ± 3.87 |
| 8 | 5.82 ± 0.39 | 6.07 ± 0.49 | 19.92 ± 3.23 | 21.00 ± 3.26 |
| 12 | 6.02 ± 0.51 | 6.22 ± 0.74 | 20.62 ± 0.64 | 19.32 ± 1.72 |
| 2. Effect of rhein on the kidney weight at the 12th week | | | | |
| Kidney Weight (grams) | 0.84 ± 0.09 | 0.72 ± 0.11 | 1.31 ± 0.73 | 0.93 ± 0.13 |
| Kidney Volume (ml) | 0.794 ± 0.019 | 0.804 ± 0.210 | 1.083 ± 0.049 | 0.834 ± 0.109 |
| Kidney Index ($\times 10^{-3}$) | 3.33 ± 0.21 | 4.04 ± 0.39 | 7.21 ± 1.30 | 4.76 ± 0.76 |

EXAMPLE 2

Suppression of Renal Hypertrophy by Sodium Rheinate in Experiment Diabetic Rats

Drug: aqueous solution of sodium rheinate at concentration of 0.1 g/L for oral

Diabetic animal model of rat: Adult female SD rats (Experimental Animal Center, Jinling Hospital, Nanjing) with body weights of 200 to 250 grams were used. Rats were made diabetic by an intra-abdominal injection of Streptozotocin (Sigma Chemical Co.; in 0.1 mmol/L citrate buffer, pH 4.5) in a dose of 25 mg/Kg/day for 5 days. Only rats with blood glucose level within the range of 13 to 25 mmol/L were recognized as the establishment of the diabetic mode.

The observation was focused on the changes of kidney weight and volume in diabetic rats treated by rhein.

The experiment was designed as the following:

|  | Normal rats | | Diabetic rats | |
| --- | --- | --- | --- | --- |
|  | Control | Rhein-treated | Control | Rhein-treated |
| No. of animals | 6 | 5 | 6 | 6 |
| Dosage of Rhein-Na, mg/Kg/day | 0 | 1 | 0 | 1 |
| Distilled water, ml/Kg/day | 5 | 5 | 5 | 5 |

The experimental results are listed in the following tables.

|  | Normal rats | | Diabetic rats | |
| --- | --- | --- | --- | --- |
|  | Control | Rhein-treated | Control | Rhein-treated |
| 1. Effect of sodium rheinate on the changes of the blood glucose levels (mmol/L) | | | | |
| Pre-diabetic | 5.33 ± 0.54 | 6.06 ± 0.72 | 6.12 ± 0.84 | 6.17 ± 1.01 |
| After diabetic (weeks) | | | | |
| 1 | 6.22 ± 0.74 | 6.52 ± 0.74 | 22.16 ± 3.64 | 21.82 ± 2.69 |
| 4 | 5.88 ± 0.66 | 6.48 ± 0.77 | 21.57 ± 3.99 | 19.97 ± 4.17 |
| 2. Effect of sodium Rheinate on the kidney weight (g) at the 12th week | | | | |
| Kidney Weight (grams) | 0.66 ± 0.11 | 0.59 ± 0.09 | 0.89 ± 0.22 | 0.71 ± 0.20 |
| Kidney Index ($\times 10^{-3}$) | 4.13 ± 0.09 | 4.34 ± 0.37 | 7.94 ± 1.73 | 5.68 ± 1.16 |

EXAMPLE 3

Clinical Trial of Rhein on Diabetic Nephropathy

Twenty-five diabetic patients diagnosed according to the standard of WHO where enrolled in this study. The fast blood glucose levels were above 250 mg/100 ml in these patients. Diabetic nephropathy was confirmed morphologically by renal biopsy, or with measurement of urinary protein or albumin excretion in each patient.

A yellow powder supplied in capsule containing 25 mg rhein. The dosage of 100 mg per day (50 mg twice a day) rhein was given orally as therapy. All patients were followed at regular intervals for measurement of serum creatinine values and urinary protein or albumin excretion at least for 3 months.

The experiment results are listed as the following:

1. General clinical data

All patients enrolled into this study tolerated rhein treatment. None of the recipients receiving rhein at dose of 100 mg per day had gastro-intestinal reactions as vomiting, diarrhea et al.

There is no liver function abnormally and deterioration of renal function in patients treated with rhein. Blood routine test is normal.

2. Changes of urinary protein excretion

Of twenty-five diabetic patients given rhein treatment, 18 patients (72%) had obvious decrement of urinary protein excretion during the three months therapy. There are seven diabetic patients with no change or increase of urinary protein excretion. The datum are shown in the following table:

| Change of urinary protein excretion | Treatment after 3 months (No.) |
|---|---|
| No change | 7 |
| Decrease of 25% | 5 |
| Decrease of 50% | 9 |
| Decrease of 75% | 4 |

By clinical trial, rhein could decrease the urinary protein excretion in diabetic patients treated by rhein. It is suggested that the medicine possesses therapeutic effect on the kidney damage in diabetic nephropathy, and can be used in clinical practice of diabetes.

INDUSTRIAL APPLICATION

The medicine provided by the present invention can be easily absorbed from gastro-intestinal trace, decreased the urinary protein excretion in diabetic patients treated, obviously reduce kidney index. It can be prepared into oral capsule or oral aqueous solution for the clinical treatment of diabetic nephropathy.

We claim:

1. A method for treating diabetic nephropathy which comprises administering to a subject in need of such treatment an effective diabetic nephropathy amount of a composition comprising rhein of a general formula

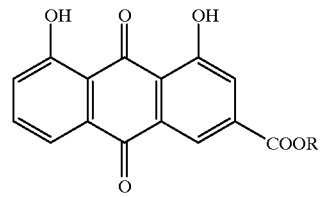

wherein R represents hydrogen, sodium or potassium.

2. The method in accordance with claim 1, wherein the said composition contains sodium rheinate or potassium rheinate.

3. The method in accordance with claim 1, wherein the said composition is supplied in a capsular form or aqueous solution for oral administration.

4. The method in accordance with claim 1, 2 or 3, wherein the dosage of the said rhein or the salt thereof is not larger than 200 mg/day when the said composition is orally administered.

* * * * *